(12) United States Patent
Rejndrup

(10) Patent No.: US 7,912,864 B2
(45) Date of Patent: Mar. 22, 2011

(54) RETRIEVING COLLECTED DATA MAPPED TO A BASE DICTIONARY

(75) Inventor: Kim Rejndrup, Needham, MA (US)

(73) Assignee: Oracle International Corp., Redwood Shores, CA (US)

( * ) Notice: Subject to any disclaimer, the term of this patent is extended or adjusted under 35 U.S.C. 154(b) by 577 days.

(21) Appl. No.: 11/861,237

(22) Filed: Sep. 25, 2007

(65) Prior Publication Data

US 2009/0083218 A1    Mar. 26, 2009

(51) Int. Cl.
*G06F 17/30*    (2006.01)
*G06F 7/00*    (2006.01)

(52) U.S. Cl. ............ 707/793; 705/2; 707/763; 707/765; 707/769

(58) Field of Classification Search .................. None
See application file for complete search history.

(56) References Cited

U.S. PATENT DOCUMENTS

| | | | | |
|---|---|---|---|---|
| 5,963,938 A * | 10/1999 | Wilson et al. | ......................... | 1/1 |
| 6,684,221 B1 * | 1/2004 | Rejndrup | ............................. | 1/1 |
| 2002/0165852 A1 * | 11/2002 | Gogolak | .......................... | 707/3 |

* cited by examiner

*Primary Examiner* — Greta L Robinson
*Assistant Examiner* — James J Wilcox

(57) ABSTRACT

A method includes defining a plurality of terms for use in conjunction with a study where the terms are stored according to a series of relations and the relations corresponding to the terms indicate an association from a term to at least one other of the plurality of terms, defining at least one group of terms taken from the plurality of terms and storing at least one group of terms, including the relations corresponding to each term, defining a further level of relations to be applied to the group of terms, the further level of relations defining inclusion and exclusion criteria, and providing a match term defined by the group of terms and querying a memory of data from the study to find occurrences of the match term as defined by the further level of relations.

11 Claims, 9 Drawing Sheets

301 Filter Dictionary — Filter Dictionary Of → 303 Base Dictionary

304 High Level — Named Relations / Related to → High Level 306

305 Lower level — Associate / Pseudo parent / Broad → Coding Level 307

307A-307D

VT Level 308

Narrow Terms
Cullen's sign
Hereditary pancreatitis
Oedematous pancreatitis
Pancreatic abscess
Pancreatic haemorrhage
Pancreatic necrosis
Pancreatic phlegmon
Pancreatic pseudocyst
Pancreatic pseudocyst drainage
Pancreatitis acute
Pancreatitis acute on chronic
Pancreatitis haemorrhagic
Pancreatitis necrotising
Pancreatitis NOS
Pancreatitis relapsing
Pancreatorenal syndrome

502

Signs and symptoms relevant for pancreatitis (Broad)
Abdominal distension
Abdominal pain NOS
Abdominal pain upper
Abdominal rebound tenderness
Abdominal rigidity
Abdominal tenderness
Acute abdomen
Ascites
Blood bilirubin increased
Bowel sounds abnormal
Fat necrosis NOS Gastrointestinal pain NOS
Haemorrhagic ascites
Hyperbilirubinaemia
Ileus paralytic
Jaundice NOS
Nausea
Peripancreatic fluid collection
Vomiting NOS
Vomiting projectile

504

Lab values relevant for pancreatitis (Broad)
Blood amylase abnormal
Blood amylase increased
Lipase abnormal
Lipase increased
Lipase urine increased
Pancreatic enzyme disorder NOS Pancreatic enzymes NOS abnormal Pancreatic enzymes NOS increased
Urine amylase abnormal
Urine amylase increased

506

A case of Acute Pancreatitis = Narrow term OR (Sign/Symptom AND Relevant Lab Value)

FIG. 5

RETRIEVING COLLECTED DATA MAPPED TO A BASE DICTIONARY

BACKGROUND

1. Field

The disclosed embodiments generally relate to thesaurus management systems and in particular to searching for and retrieving collected data mapped to base dictionaries.

2. Brief Description of Related Developments

In many industries, a variety of terms are used as labels for products, concepts, parts, ingredients, procedures, milestones, and other labels commonly used in the industry or within a particular company. Often, such terms are applied inconsistently, either from subtle permutations, the use of a more specific or more general term, and errors. The use of a thesaurus of terms can be beneficial in the determination of equivalent and related terms. Such a thesaurus can be queried to find an equivalent term so that consistent term usage can be applied across the industry or company.

For example, studies or trials, such as clinical studies, are often undertaken during preparation of a new consumer product. Such studies are used to determine adverse effects, effectiveness, marketability, duration, and other aspects of the new product. In the health and pharmaceutical industries, clinical studies are often mandated and scrutinized by Federal and state governmental regulations prior to the release of a new pharmaceutical or medical product. Typically, a large quantity of clinical data is generated by such studies and the clinical data is provided from a number of different sources involved with the study. The source of the data may be from human test subjects, physician reports, drug dispensary logs, laboratory test results, and other sources. The clinical data is then entered and analyzed, typically from a text format.

Pharmaceutical companies that develop new drugs are required to produce reports that show that each new drug does not harm individuals who use it. The data used to produce these reports is often hard to analyze because it is collected as freeform text. The data can include adverse events in a patient's health and corresponding medical procedures, the medications a patient received during treatment, and diagnoses. This document refers to the freeform text data collected in studies and trials as verbatim terms.

Verbatim terms are difficult to process because the terminology used across a single study or across different but related studies can vary. For example, different investigators may tend to use different terms for the reporting or recording of the same or very similar medical conditions. Thus, one or more different terms may be used to report the same condition or related conditions. But reporting, grouping and further analysis of verbatim terms require the use of consistent terminology. If different terms are used to describe the same condition, it is difficult to collect accurate data related to the condition, unless all of the possible terms are searched. If each term is not searched, all of the representative cases may not be collected and analyzed. In studies where there are many cases, the collected data may not then present an accurate analysis of data related to a particular test, condition or trial.

Several vendors, such as WHO, publish dictionaries that can be used in processing verbatim terms. However, dictionaries can only partially process the data. Dictionaries cannot take misspellings, term mutations and entirely new terms—such as new drugs—into account. An analysis simply based on matches between the dictionary terms and the verbatim terms may not be usable. This document refers to verbatim terms that do not match a dictionary term as thesaurus omissions.

When a trial or study is conducted the entered data is mapped to one or more dictionaries. In a clinical study, the entered data is mapped to one or more medical dictionaries for further analysis and data retrieval. One example of such a medical dictionary is MedDRA. When the mapping of the data is complete, the dictionaries can be used to search and analyze the collected data. Standardised MedDRA Queries (SMQ) were developed by the Council for International Organizations of Medical Sciences (CIOMS) to provide a standard way to search collected data for a given condition. Standardised MedDRA queries are groupings of MedDRA terms that relate to a specific medical condition or area of interest. The queries include terms that can related to signs, symptoms, diagnoses, physical findings, laboratory and other test data, for example. Standardised MedDRA queries are essentially another dictionary that can be superimposed on top of MedDRA for search purposes.

The ORACLE™ Thesaurus Management System (TMS) addresses the complexities associated with managing global thesauri. One of the most time-consuming tasks with development processes, such as drug development, is the classification of verbatim terms to permit deriving the standard terms for use in analysis from the free text originally captured. Many dictionaries exist for different types of information. The organization of these dictionaries, their organization and defined hierarchies can vary considerably. Presently, the searching of a dictionary in a specific manner for a given condition can require manual combining of ad-hoc queries or writing a specific program, which is cumbersome and time-consuming.

It would be advantageous to provide a global facility to standardize terminology use across dictionaries, computer applications, time and organizations. It would also be advantageous to provide a centralized, globally available repository of dictionary terms and associated verbatim terms, where information in the repository is accessible through advanced searching and classification algorithms. It would also be advantageous to provide a retrieval tool to accompany a repository of dictionary terms that allows for the retrieval of data that have no obvious linguistic relationship.

SUMMARY

In one aspect, the disclosed embodiments are directed to a method. In one embodiment the method includes defining a plurality of terms for use in conjunction with a study where the terms are stored according to a series of relations and the relations corresponding to the terms indicate an association from a term to at least one other of the plurality of terms, defining at least one group of terms taken from the plurality of terms and storing at least one group of terms, including the relations corresponding to each term, defining a further level of relations to be applied to the group of terms, the further level of relations defining inclusion and exclusion criteria, and providing a match term defined by the group of terms and querying a memory of data from the study to find occurrences of the match term as defined by the further level of relations.

In another aspect, the disclosed embodiments are directed to a method. In one embodiment, the method includes defining a plurality of clinical terms for using in conjunction with a clinical study, storing the plurality of clinical terms in a memory according to a series of relations, defining a plurality of relations corresponding to the clinical terms, the plurality of relations indicative of an applied association from one clinical term to at least one other clinical term in the plurality of clinical terms, storing the relations in the memory, defining one or more terms from the plurality of terms and storing the one or more terms in a storage facility according to the plurality of relations, defining a search algorithm to be used with the one or more defined terms, and querying the memory according to the search algorithm to find at least one derived term from the relations corresponding to the one or more defined terms.

In a further aspect, the disclosed embodiments are directed to a system. In one embodiment, the system includes a memory operable to store terms according to a hierarchy of relations for a study, a relation table included in the memory and having stored therein relations indicative of an association from a clinical term to at least one other of the clinical terms, a data retrieval device coupled to the relation table configured to group selected terms from the memory and their relations, map a search criteria to the group and search for terms in the study according to the search criteria.

In another aspect, the disclosed embodiments are directed to a computer program product stored in a memory. In one embodiment, the computer program product includes a computer useable medium having computer readable code means embodied therein for causing a computer to execute a search for data in a study. The computer readable code means in the computer program product includes computer readable program code means for causing a computer to define a plurality of terms for use in conjunction with the study where the terms are stored according to a series of relations and the relations corresponding to the terms indicate an association from a term to at least one other of the plurality of terms, computer readable program code means for causing a computer to define at least one group of terms taken from the plurality of terms and storing at least one group of terms, including the relations corresponding to each term, computer readable program code means for causing a computer to define a further level of relations to be applied to the group of terms, the further level of relations defining inclusion and exclusion criteria, and computer readable program code means for causing a computer to provide a match term defined by the group of terms and querying a memory of data from the study to find occurrences of the match term as defined by the further level of relations.

BRIEF DESCRIPTION OF THE DRAWINGS

The foregoing aspects and other features of the disclosed embodiments are explained in the following description, taken in connection with the accompanying drawings, wherein:

FIG. 5 is an illustration of a term table that can be used in conjunction with the disclosed embodiments.

DETAILED DESCRIPTION OF THE PREFERRED EMBODIMENT(S)

Figure 1:
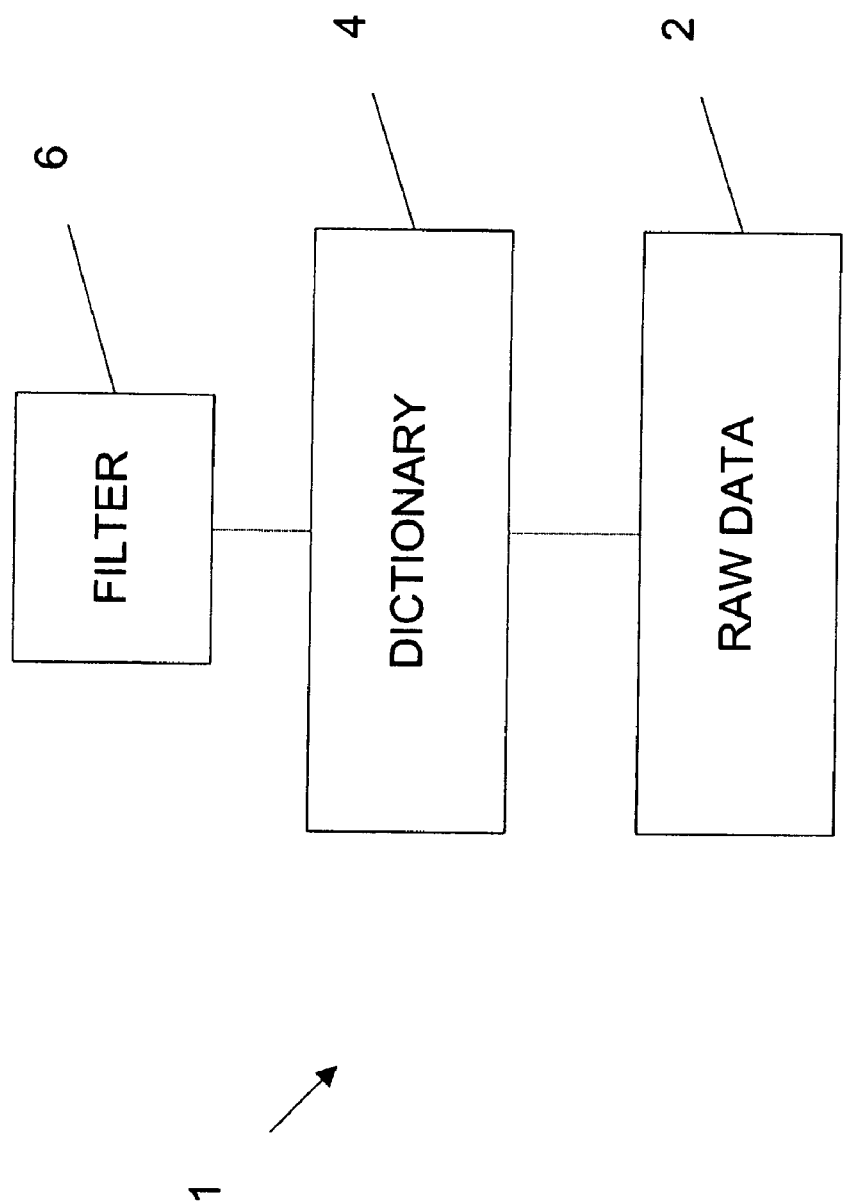
FIG. 1 is a block diagram of a system incorporating features of the disclosed embodiments.

Referring to FIG. 1, a block diagram of one embodiment of a system 1 incorporating features of the disclosed embodiments is illustrated. Although the embodiments disclosed are described with reference to the embodiments shown in the drawings, it should be understood that the embodiments disclosed can be embodied in many alternate forms of embodiments.

The disclosed embodiments generally relate to a data retrieval tool, referred to herein as a filter dictionary, that can be added to or superimposed on any dictionary, in for example, a thesaurus management system. The retrieval tool of the disclosed embodiments will allow the accessing and retrieval of data using groupings of terms and concepts that relate to a defined condition or area of interest. In one embodiment, concepts and relations between the concepts and terms are carried over to the retrieval tool from the underlying source data repository. In alternate embodiments, the user can create a repository in the retrieval tool where terms which do not have any existing relationships are linked and mapped together to allow for searching and retrieval of data that do not share direct stored relationships.

A thesaurus of terms employed in an industry, enterprise, or company allows terms common to the industry, enterprise, or company to be associated with other related or equivalent terms. Associations between the terms can be organized in a hierarchy. Such associations indicate relations between the terms, which can include for example, more general terms, more specific terms, and equivalent terms. By querying the hierarchy of terms, a particular term can be classified to another term. Such classification facilitates consistent term usage throughout the various contexts in which the term is employed. These contexts may include research reports, product literature, marketing literature, technical specifications, and corporate policies. For example, when storing concepts and mapping relations between concepts, as described for example in U.S. Pat. No. 6,684,221, a user can store the term "Acid-base disorders". Relationship links from the term "Acid-base disorders" to "Metabolic acidosis (excl diabetic acidosis)" and "Hyperlactacidaemia" can be established, as the concepts are known to have certain relevant relations. The user can then execute a search of raw data in a study for occurrences of the term "Acid-base disorders". The search would also find all the children of the term "Acid-base disorders", as defined by the relation links noted above.

The retrieval tool of the disclosed embodiments allows for the grouping of terms that relate to a condition, concept or area of interest. The groupings can be defined by definitions, inclusion and exclusion criteria. In one embodiment, one or more algorithms can also define the groupings. In some cases, it will aid in case identification if the user applies an algorithmic approach to the terms in the retrieval tool or filter and selecting cases based on a defined combination of selected terms. The groupings can include a mixture of more specific terms and less specific terms that are generally consistent with a description of the overall syndrome or concept associated with events and data related events. The retrieval tool of the disclosed embodiments can be used to identify cases or events that are highly relevant to the condition or concept of interest (a "narrow" search), as well as to identify all possible cases or events that may have some bearing on the condition or concept of interest (a "broad search").

Referring to FIG. 1, for example, when a trial or study is completed, the raw data 2 from the study, or terms, can be mapped to one or more dictionaries 4. When the mapping is complete, the dictionary(s) 4 can be used to search and analyze the raw data 2. A filter dictionary 6 is superimposed on top of the base dictionary 4. As will be described herein, the addition of the filter dictionary 6 will allow for the collection of clinical data via a pre-defined and deterministic set of mappings between the filter dictionary 6 and its base dictionary 4. The filter dictionary 6 of the disclosed embodiments allows for the identification of complex data conditions in seemingly unrelated clinical data. Prior to this, sets of ad-hoc queries would have to be manually combined, or specific programs developed. In the disclosed embodiments, the filter dictionary 6 includes a series of relationships between dictionary terms. In this way, the user can retrieve data from the clinical study data 2 in a pre-determined fashion, which could not otherwise be done with a set of queries. The disclosed embodiments also provide for the defining of new queries by creating new relationships between a term in the filter tool 6 and terms in the base dictionary 4. This makes the searches of the raw data 2 more efficient and simplifies the enforcement of standard searches.

The filter dictionary 6 of the disclosed embodiments is a term retrieval tool that superimposes a search structure, in the form of groupings of terms, on an existing base dictionary 4. The grouping of terms in the filter dictionary 6 can be based on different scope and contexts, and algorithms can be used to define searches based on the combination of terms and other defined attributes. Unlike a base dictionary, such as MedDRA, the filter dictionary 6 of the disclosed embodiments does not define terms. Rather, the filter dictionary 6 of the disclosed embodiments will define groupings of existing terms from a specific version of a base dictionary 4. The term groupings can be used to search though volumes of data to ultimately filter out cases or studies for the target search criteria or area of interest. Prior to this, it was very time consuming and error prone to write programs to find relevant clinical data from the raw data 2. Because the relevant data is often spread across several categories, it is not always possible to find the data via simple text comparison and matching. Current thesaurus systems and base dictionaries only define or classify different clinical terms as corresponding to common clinical terms. One example of such a system is disclosed in U.S. Pat. No. 6,684,221, owned by Oracle International Corporation, the disclosure of which is incorporated herein by reference in its entirety.

Figure 2:
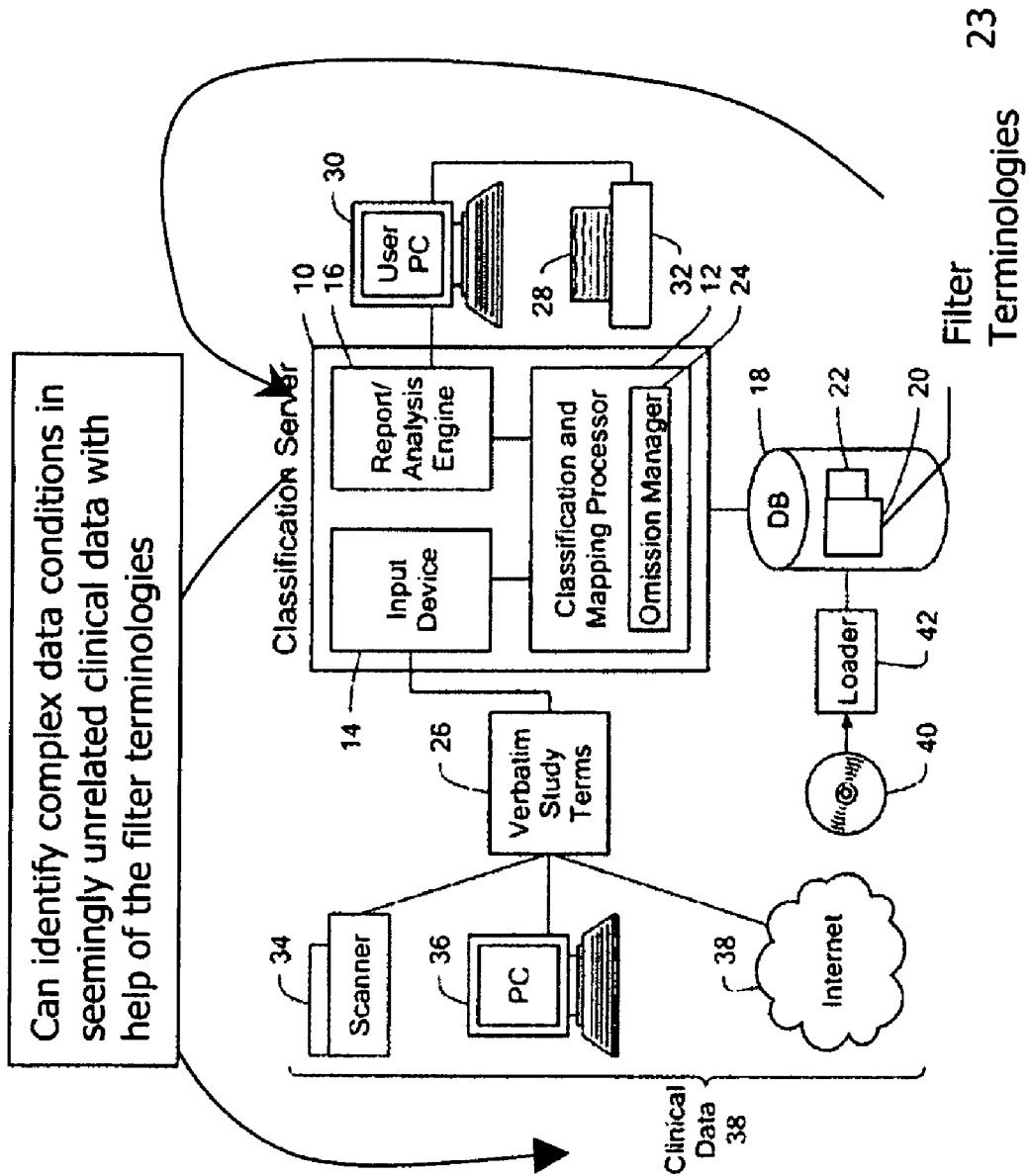
FIG. 2 is a block diagram of a system incorporating features of the disclosed embodiments.

FIG. 2 shows a block diagram of one embodiment of a classification and mapping system. A classification server 10 has a classification and mapping processor 12, an input device 14, and a report/analysis engine 16. The classification and mapping processor 12 is in communication with a thesaurus database 18, which stores the clinical terms and relations. The thesaurus database 18 of the disclosed embodiments includes a content table 20, a relation table 22 and a filter terminology table 23. In one embodiment, the content table 20 and the relation table 22 can be combined to form the base dictionary 21. The content table 20 stores the clinical terms and the relation table 22 stores the relations defining associations between the clinical terms. The filter terminologies table 23 stores groupings of terms and relations taken from the content table 20.

In one embodiment, the terms that are used by the filter dictionary or termininolgies table 23 are terms stored in the content table 20. The relationships or relations between the terms used by the filter dictionary 23 are stored in the relation table 22. In one embodiment, the relationships between the terms used by the filter dictionary 23 and the base dictionary 21 are stored in the relation table 22 as well. The classification and mapping processor 12 also includes an omission manager 24 for resolving terms not found to match the clinical terms in the content table 20.

In a typical study, verbatim study terms 26 are extracted from raw clinical data by a variety of methods, and provided to the input device 14. The classification and mapping processor 12 receives the verbatim study terms 26 as match terms from the input device 14, and attempts to classify the match terms according to corresponding clinical terms in the thesaurus database 18, as described further below. The clinical terms are initially transmitted to the thesaurus database 18 from an external media source, such as a CD-ROM 40, from a loader 42. The classification results are sent to the report/analysis engine 16, where an output report is produced from the classification results. The output report 28 is sent to the user PC 30, where it may be printed via the attached printer 32. Alternatively, the output report 28 is received by an application running on the user PC 30 for further processing by any suitable method, such as correlation with previous reports, sorting, or statistical analysis. Examples of the classification process are described in U.S. Pat. No. 6,684,221.

The verbatim study terms 26 are provided from clinical data 38 by any suitable method, including the scanner 34 from hardcopy data reports, the PC 36 from a data entry or other suitable application, or a public access network such as the Internet 38 via an HTML browser or other format. The raw, unprocessed clinical data 38 is then interrogated for verbatim study terms 26 to provide to the input device 14 for classification. In a particular embodiment, the raw, unprocessed clinical data 38 is received by a clinical study data management application executing on the PC 36, such as ORACLE.RTM. CLINICAL, commercially available from Oracle Corporation of Redwood Shores, Calif.

In a clinical study, the clinical terms are stored in the thesaurus database 18. In a typical study, the thesaurus database 18 may, for example, include 200k clinical terms in the content table 20 and 400k relations in the relation table 22. As indicated above, an external media source is often employed to populate the initial thesaurus database 18. Typically, external media sources are purchased in the form of a dictionary on CD-ROM 40 from an external vendor. Common vendor-supplied dictionaries include WHO-Drug (World Health Organization Drug Dictionary) by the World Health Organization, COSTART (Coding Symbols for a Thesaurus of Adverse Reaction Terms) by the Drug Information Association, MSSO (MedDRA Maintenance and Support Services Organization) and CPT (Current Procedural Terminology) by the American Medical Association. Other vendors and dictionaries are common and known in the industry.

Figure 3:
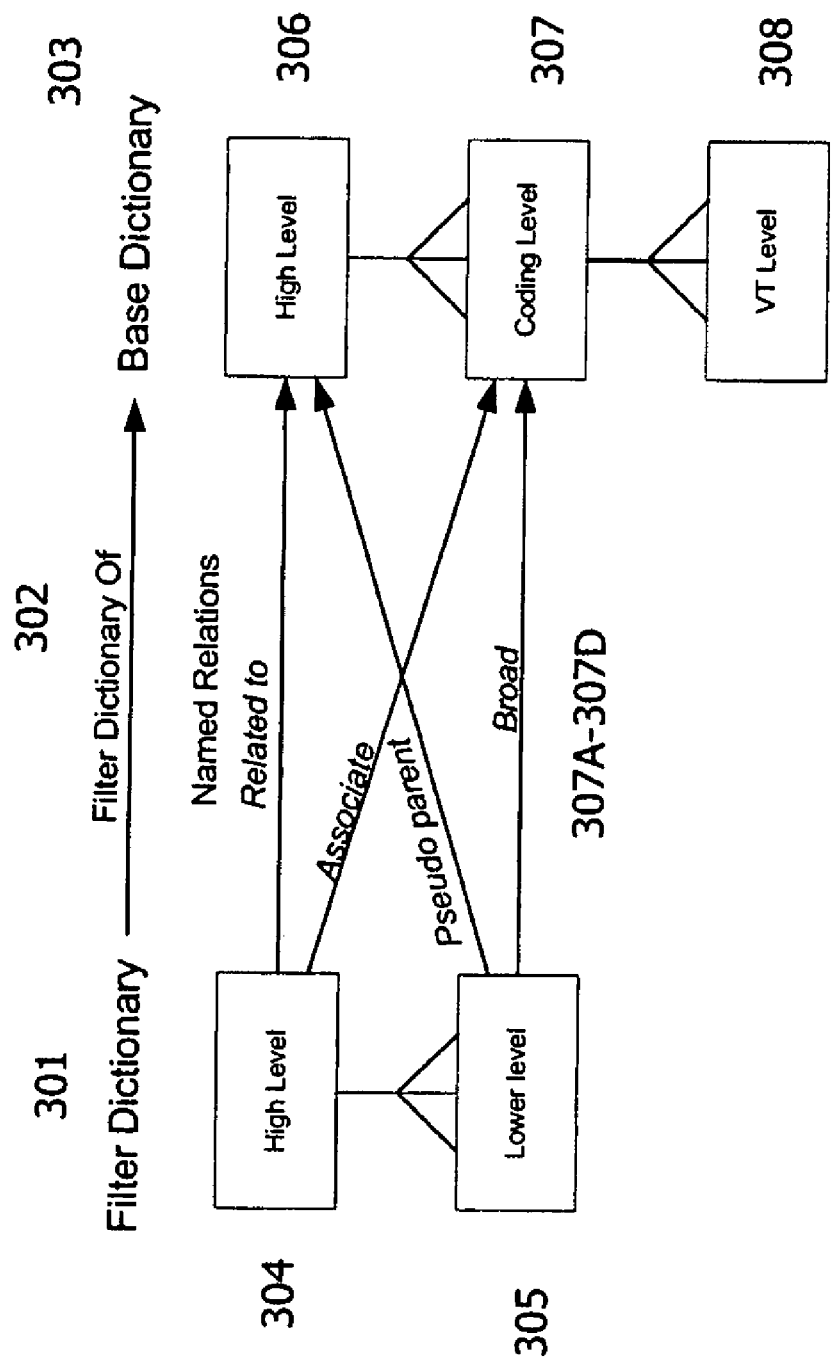
FIG. 3 is a block diagram illustrating aspects of the disclosed embodiments.

The filter terminologies table 23 stores groupings of terms and relations taken from the base dictionary 21, referred to herein as a filter dictionary, that are defined by unique attributes and properties. For example, in the embodiments described herein, the filter dictionary 23 can have one and only one link to a base dictionary. Referring to FIG. 3, this can be called for example, a "Filter Dictionary Of" dictionary link 302. The link 302 from the filter dictionary 301 to the base dictionary 303 defines that the filter dictionary 301 will only contain terms that are defined in the base dictionary 303. Similarly, a base dictionary 303 will have one and only one link 302 to a filter dictionary 301.

Filter dictionaries can also have associated virtual dictionaries. These virtual dictionaries, which may be versions of the filter dictionary, must have the same cut-off date as an existing virtual dictionary of the filter dictionary's base dictionary. As described herein, the filter dictionaries of the disclosed embodiments are defined as a strong type, which generally means that the terminology structure is pre-defined. In some cases terminologies can have structures that are defined by the data itself. The filter dictionary can also have the same language attribute as the base dictionary. Thus, if the base dictionary stores term in English, the filter dictionary terminology will also be stored in English. In alternate embodiments, any suitable language can be used, other than including English. The filter dictionary of the disclosed embodiments cannot have a verbatim term level.

The filter dictionary of the disclosed embodiments must also be automatically mapped to the same domains as the base dictionary. For example, if MedDRA SMQ is a filter dictionary of MedDRA, and MedDRA is mapped to domains A and B, MedDRA SMQ must also be mapped to domains A and B automatically. Similarly, a virtual dictionary of a filter dictionary must be mapped to the same domains as its base virtual dictionary. Verbatim terms can be grouped into a domain and the coding within a domain has to be consistent. For example, in one domain, the term "Bad Headache" is a verbatim term associated with the term or condition "migraine." However, in another domain the term "Bad Headache" could map to the term or condition "Sinus Headache". Generally a domain relates to the field to which the studies or trials relate. For example, a domain may relate to the therapeutical area in the world of clinical trials, with reference to the medicine and pharmacology. Since domains for filter dictionaries cannot be maintained directly, whenever a change is made to the dictionary domain definition of a base dictionary, the domain dictionary definition of the filter dictionary will be synchronized, automatically.

For example, referring again to FIG. 3, one example of the relationships between a filter dictionary 301 and a base dictionary 303 according to the disclosed embodiments is illustrated. A dictionary link 302 is created linking the filter dictionary 301 to the base dictionary 303. In one embodiment, the filter dictionary 301 includes high level terms 304 and lower level terms 305. The base dictionary 303 includes high level terms 306, coding level terms 307 and a verbatim term level 308. The coding level implies that verbatim terms are mapped to this level. As shown in FIG. 3, the filter dictionary 301 does not include a verbatim term level. Named relation links 307a-307d are defined between the filter dictionary 301 and the base dictionary 303. These include for example, Related to Term Link 307a, Associate Term Link 307b, Pseudo Parent Term Link 307c and Broad Term Link 307D The Related To Term Link 307a describes an Associate Relationship as defined by ANSI/NISO Z39.19-1993. The Associate Term Link 307B could describe an Associated etiology as defined by SMOMED. The Pseudo Parent Term Link 307C is a arbitrary relationship that would imply a certain type of relation as defined by the creator of the terminologies. The Broad Term Link 307D can be used to describe a "Broad scope" relation as defined by the filter dictionary definitions. Although only named relation links 307a-307d are shown in FIG. 3, in alternate embodiments, any suitable number of links can be defined.

In one embodiment, when the Named Relation links 307A-307D between the filter dictionary 301 and base dictionary 303 are defined or created, the filter dictionary 301 inherits all of the meta-data definition attributes of the base dictionary. These links ensures that all of the relationships between terms in the base dictionary are valid between the two structures. (the filter dictionary 301 and the base dictionary 303.) Relationships, as that term is used herein, can include for example broad scope relations and narrow scope relations. For example, the named relations, Broad Scope and Narrow Scope, provide the ability to define broad scope terms and narrow scope terms for a filter dictionary.

Figure 4:
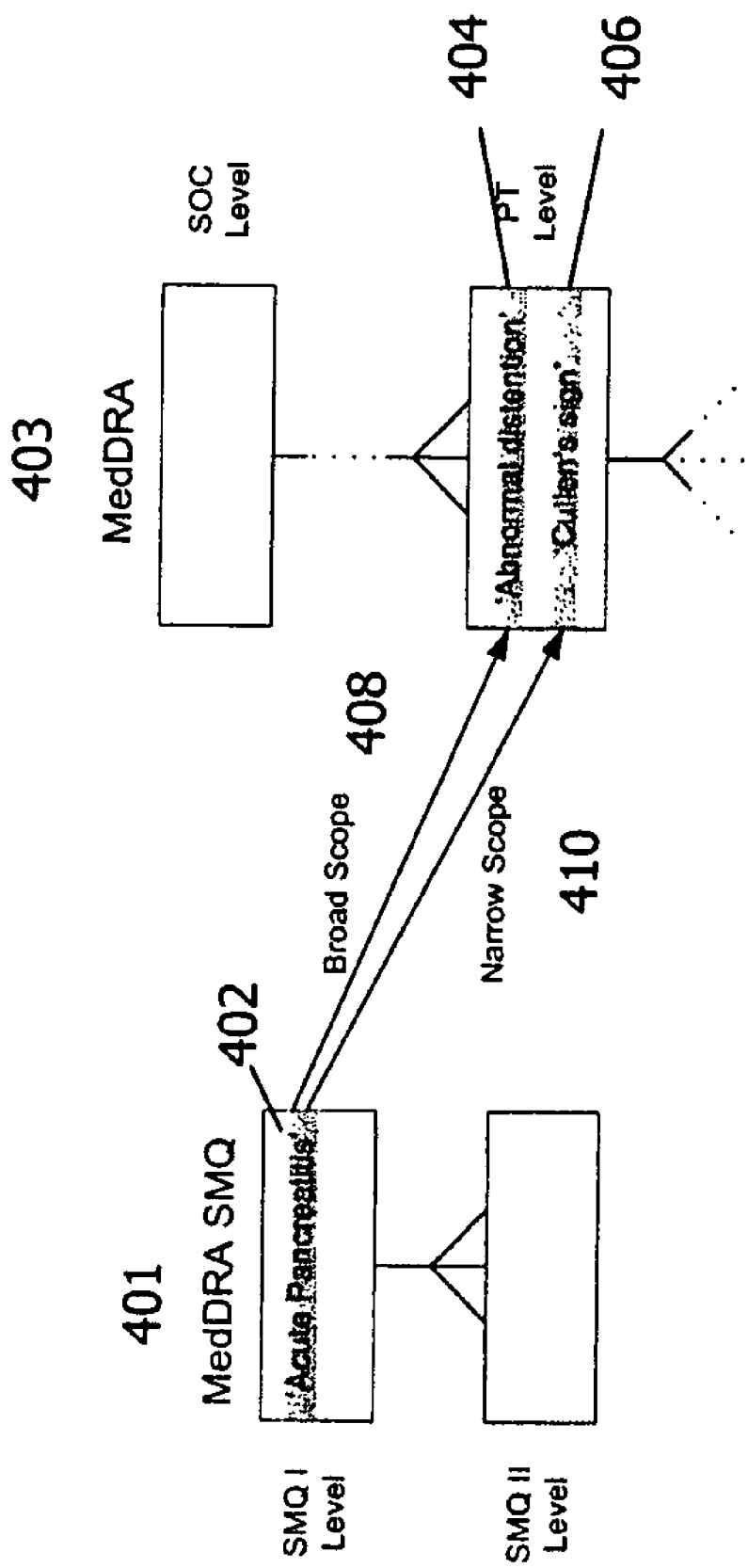
FIG. 4 is a block diagram illustrating aspects of the disclosed embodiments.

As an example, referring to FIG. 4, consider the term "Acute Pancreatitis" 402, which is linked to or stored in the filter dictionary 401. In this example, the term "Acute Pancreatitis" is selected from the content table 22 shown in FIG. 1. Relationships between this term "Acute Pancreatitis" and other terms in the content table 22 are defined. A broad scope term link 408 is created and defined to bind the term "Acute Pancreatitis" with "Abnormal Distension." A narrow scope term link is defined between the term Acute Pancreatitis 402 in the filter dictionary 401 and the term "Cullen's Sign 406 in the base dictionary 403. The links 408 and 410 are the named links that create a relation between two terms and bind the data in the filter dictionary 401 with the base dictionary 403. Thus, in the example shown in FIG. 4, a links 408 and 410 are created between the term "Acute Pancreatitis" 401 in the filter dictionary 401 to the preferred term ("PT") "Abnormal distention" 404 in the base dictionary 403, as a broad scope term relation, and between the PT "Cullen's sign" 406 as a narrow scope term relation. These relations can be part of the Filter dictionary data provided.

Each filter dictionary can implement specific design features that define the utility of the filter dictionary and several criteria can contribute to the scope context of a search term. In one embodiment, the filter dictionary will be defined as a grouping of dictionary terms based on a specific version of the base dictionary. The base dictionary terms can be defined as having a broad scope relation to a term in a filter dictionary query or a narrow scope relation to a term in a filter dictionary query. The base dictionary terms can be defined as meeting certain conditions within the relationship of a named scope. For example, grouping of base dictionary terms mapped to a filter dictionary can be identified as having a specific context. For example, as discussed above, these can include "broad" context or a "narrow" context. A broad scope term can have applicability across a number of different cases and a "broad" context search will return a result set that lists all cases that meets the specific search criteria or area of interest. In some cases the search result set for a broad search might include terms that are of little or no interest to the search criteria. A "narrow" context search will return a result set that include terms identifying or related to cases that are highly likely to meet or represent the specific search criteria or area of interest. In alternate embodiments, any suitable relationship scope can be defined. The disclosed embodiments allows the user to define any scope or "context", such as for example narrow, wide, unique or anything related.

For example, referring to FIG. 5, a named scope relationship table and search algorithm defined to identify cases of Acute Pancreatitis is illustrated. As shown in FIG. 5, the table illustrates sets of terms that have been mapped to the filter dictionary with different named relations. The relations defined in this table are Narrow Relations 502, Broad Relations 504 and Broad Relations 506. The first column 502 shows terms that are mapped to the filter dictionary term with a "narrow" named relation. The other columns 504 and 506 are mapped as "broad" relations, with a different subtype. In alternate embodiments, one could create three different types of named relationships, or any desired number and types of relationships. The narrow relationship set 502 includes those terms that are related to the condition "acute Pancreatitis", which is the term that is desired to be searched for. In this particular example, the user is interested in conducting a search for patients and cases that may be related to "acute Pancreatitis." Since there can be many different terms that may be indicative of this condition, a single term search may not lead to very useful search results. The disclosed embodiments allow the user to take advantage of certain relationships that are defined between and among different terms and categories of terms as shown in FIG. 5, for example. As shown in FIG. 5, the terms in the broad relationship category 504 are signs and symptoms that although may be relevant to "Pancreatitis", which by themselves, are not necessarily indicative of the particular condition. Similarly, the terms in the broad relationship category 506 are lab values relevant to or for Pancreatitis, which by themselves may not be necessarily indicative of pancreatitis. However, by establishing relationship links between and among these terms in the filter dictionary, the search result set for a case of "acute Pancreatitis" will include for example "cases or patients or. . . " with both "abdominal distension" and "blood amylase abnormal", or "Nausea" and "Lipase increased" or other similar combination of conditions as defined by the search criteria. In this example, the search criterion is defined as "Narrow term OR (Sign/Symptom AND Relevant Lab Value). Both of the terms "abdominal distension" and "blood amylase abnormal", belong in the "broad" scope relationship categories. Each term also belongs to a different category of terms within the broad scope context. The filter dictionary of the disclosed embodiments allows a user to predefine a series of relationships between dictionary terms. In this example, it is the relationships between narrow terms and broad terms. Several criteria can be used to contribute to the broad scope context of a search term. Different terms or sets of terms can fall within the broad scope context of a search term. Each category can be distinguished in a suitable manner. For example a status identifier might be provided, such as A, B or C. Referring to FIG. 5 for example, the Sign and symptoms terms 504 belong to the broad scope of a search term as do the Lab values terms 506. In one embodiment, a status identifier of "B" can be assigned to the terms in category 504 while the status identifier of "C" can be assigned to the terms in category 506. Then, the broad scope relation link 408 in FIG. A4 will correspond to the status B identifier. A relation link from the term "acute Pancreatitis" in the filter dictionary to the term "Blood amylase abnormal" will have the status "C".

Algorithms within the filter dictionary can be used to further define combinations of specific terms based on rules defined that can be processed programmatically during a search operation. One example of an algorithm description can comprise "Category A OR (Category B AND Category C)", where category B and category C can comprise different categories or status identifiers of attributes that are related to the search criteria. The algorithm term "A" can represent a narrow scope term of the search criteria. In the above example, the description can represent "Status='A' union (status='B' intersect status='C'). In alternate embodiments, any suitable algorithm description or number of algorithms can be defined and used. The search algorithm for Acute Pancreatitis in this example is in the form of Narrow Term OR (Sign/Symptom AND Relevant Lab Value). Thus, in this example, the search result set for cases of acute Pancreatitis will include those cases where a narrow category relationship term 502 is matched, or the combination of terms in category B 504 and category C 506 is matched. Although only two categories of terms are illustrated in this example, it will be understood that any suitable number of categories can be used. In one embodiment, the data retrieval tool can be used to find terms in a study that have no linguistic relationship. When there is no linguistic relationship between terms, standard search algorithms cannot be used to accurate result sets. As noted above, the typical thesaurus management system or dictionary creates links or relations between like terms. However, in some instances, certain terms may not be linked by any obvious or particular relation in the dictionary, but yet may have some commonality with respect to terms used in a particular study. The data retrieval tool of the disclosed embodiments can be used to create a dictionary that links or maps seemingly unrelated terms. The existing relations of each of these terms will be mapped to the new dictionary and a subsequent search will provide results that include these terms and their children, as defined by the relationships.

For example, consider the term "Acid-base disorders". In the base dictionary, relationship links from the term "Acid-base disorders" to its child terms "Metabolic acidosis (excl diabetic acidosis)" and "Hyperlactacidaemia" can be established, as the terms are known to have certain relevant relations. A search of raw data in a study for occurrences of the term "Acid-base disorders" will find all the children of the term "Acid-base disorders", as defined by the relation links noted above. However, consider the situation where in conjunction with the above terminology the following information was also stored. "Metabolic, nutritional and blood gas investigations"→"Blood gas and acid base analyses"→"Blood lactic acid increased". The search of "Acid-base disorders" would not return "Hyperlactacidaemia" and "Blood lactic acid increased", since the two concepts do not share terminology relations and do not share a common linguistic base.

The retrieval tool of the disclosed embodiments allows the user to classify verbatim term to concepts (dictionary terms) in the dictionary. In this situation, the following example could occur. In the study Patient 1 had an occurrence of "Hyperlactacidaemia" and patient 2 had an occurrence of "Blood lactic acid increased". However, as noted above these two terms do not share a relationship link and both would not be returned in the search results. As part of analyzing the patient data for a particular medical condition "Lactic acidosis", the user wants a query that will return both Patient 1 and Patient 2. The retrieval tool of the disclosed embodiments will allow the user to create a dictionary, which could contain more global concepts or events relating to the underlying study. In this example of patient data the concept or event category can be medical conditions. In alternate embodiments, any suitable concept can be used. In this example the term "Lactic acidosis" is added to the filter dictionary and the mapping between the term "Lactic acidosis" and the two base terminology "Hyperlactacidaemia" and "Blood lactic acid increased" is created. All underlying relationship links are automatically mapped to the filter dictionary. After this is done, the users will be able to answer questions like "find all patients with the medical condition "Lactic acidosis", which will return all cases that also include the non-obviously linked base terminology terms "Hyperlactacidaemia" and "Blood lactic acid increased."

Figure 6:
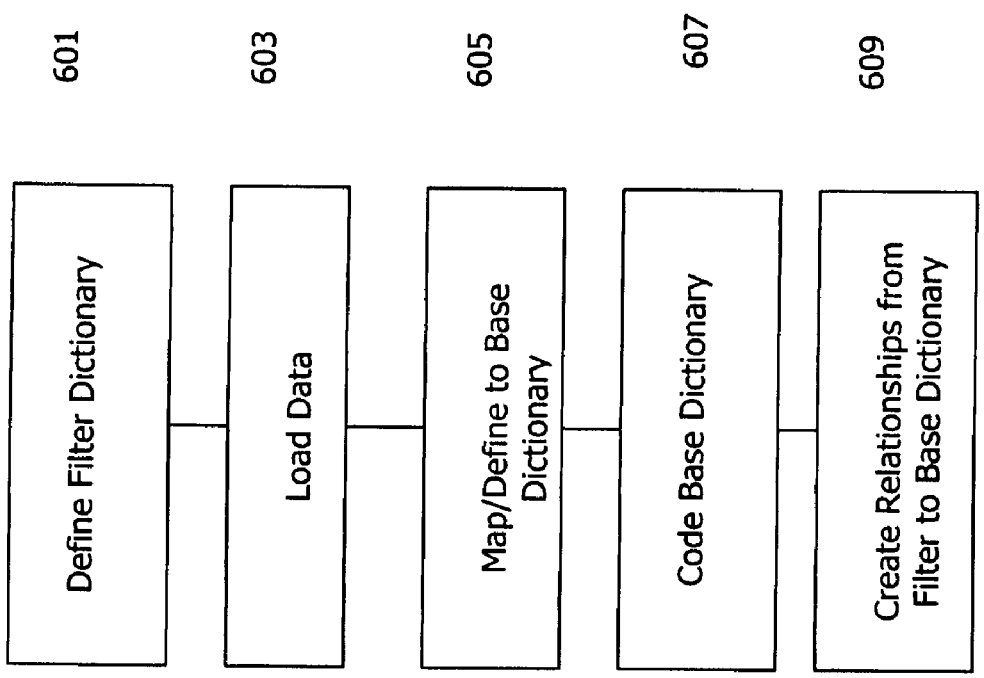
FIG. 6 is one example of a process flow of the disclosed embodiments.

Referring to FIG. 6, in one embodiment, a process according to the disclosed embodiments is illustrated. A filter dictionary is defined and created 601. Data is loaded 603 into the filter dictionary and the filter dictionary to base dictionary mapping is defined 605. In one embodiment, the filter dictionary data can be loaded simultaneously with the base dictionary data. The base dictionary is then used for coding 607. One example of coding of a dictionary is described in U.S. Pat. No. 6,684,221.

Figure 7:
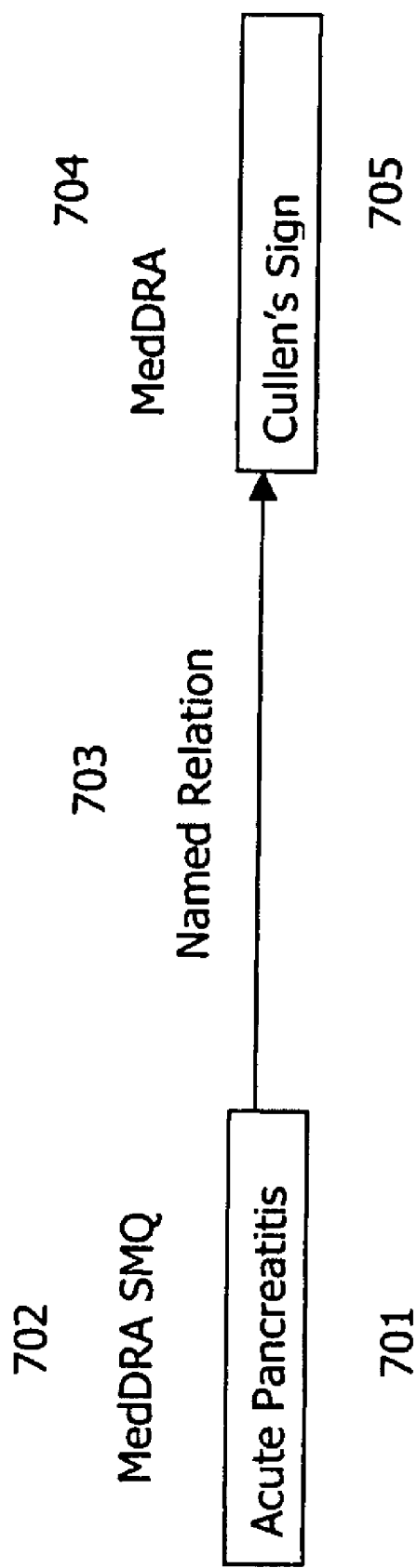
FIG. 7 is a block diagram illustrating aspects of the disclosed embodiments.

In one embodiment, grouping of search terms are defined in the filter dictionary. For each term in the base dictionary, also referred to as a member within the scope of a search term, a named relation is created 609 linking the search term in the filter dictionary to the member term in the corresponding base dictionary. For example, as shown in FIG. 7, the term "acute Pancreatitis" 701 is created or loaded into the dictionary in the filter dictionary 702 as the search term. A named relation 703 is created in the filter dictionary 702 linking the search term "acute Pancreatitis" 701 to the clinical term "Cullen's sign" 705 in the base dictionary 705, which in this example, is the MedDRA dictionary. As shown in this example, the two terms are first added to the dictionary and then the relation between terms is defined. Via a filter dictionary search, source data mapped to the base dictionary can be found. For example, in the user interface of the disclosed embodiments, the user selects the desired Filter dictionary term, in this example "acute pancreatitis" and presses the search button.

Figure 8:
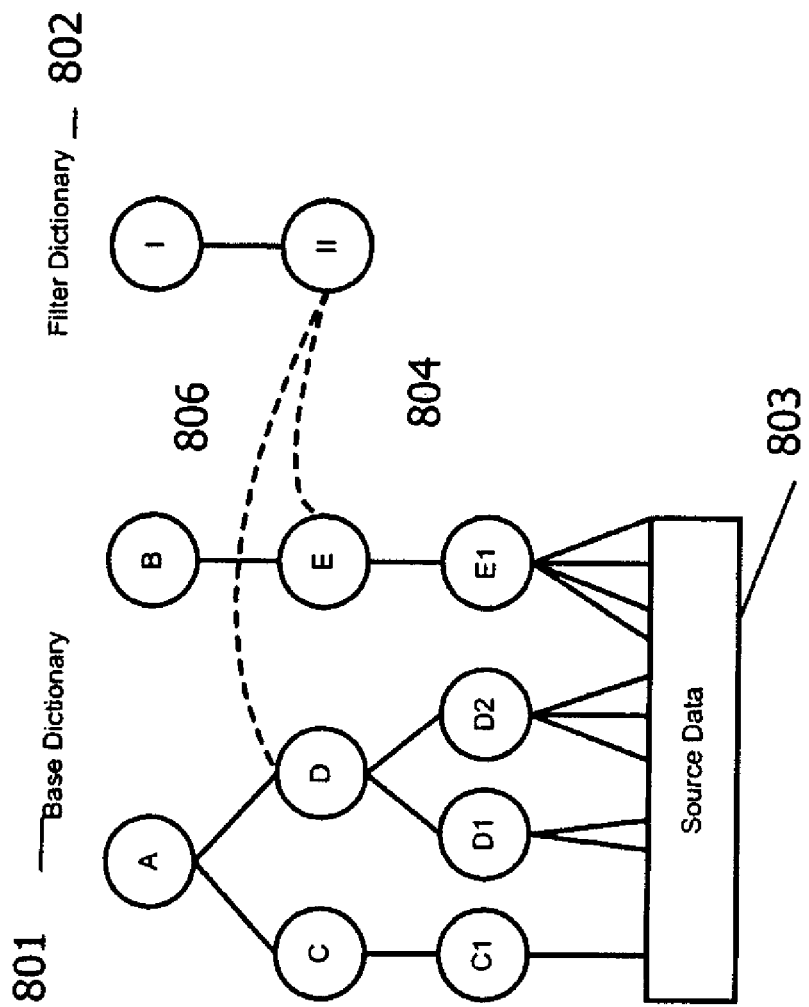
FIG. 8 is a block diagram illustrating aspects of the disclosed embodiments.

Referring to FIG. 8, when a user wants to execute a search of source data 801 using a filter dictionary 802 of the disclosed embodiments, the user will pick a starting point for the search. The starting point will be a term in the filter dictionary 802. In the examples above this term was "acute Pancreatitis", with reference to medical studies dictionaries. In alternate embodiments, any suitable term(s) can be used, with reference to the base dictionary. After the user has picked a specific term the user can specify if a hierarchical search of the terms in the filter dictionary 802 shall be used. As shown in FIG. 8., a hierarchical search would be from term I to term II or the reverse. The user will also be able to specify the name of the named relation that will be used to identify the starting points for the search in the base dictionary 803. The dotted lines 804 and 806 from Term II, to terms D and E respectively in the base dictionary 803, indicate such named relations. Since a filter dictionary search is meant to identify source data, the filter search can return verbatim terms or source data.

A verbatim term search traverses from the filter dictionary term to the terms in the base dictionary via named relations. It then drills down to the verbatim term level and returns all the verbatim terms that meet the search criteria specified by the user. Using the example in FIG. 8, suppose the terms C1, D1, D2, E1 are at the verbatim term level. A verbatim term search on the filter dictionary term 11 will return D1, D2, E1 (assuming no other search criteria is specified).

Figure 9:
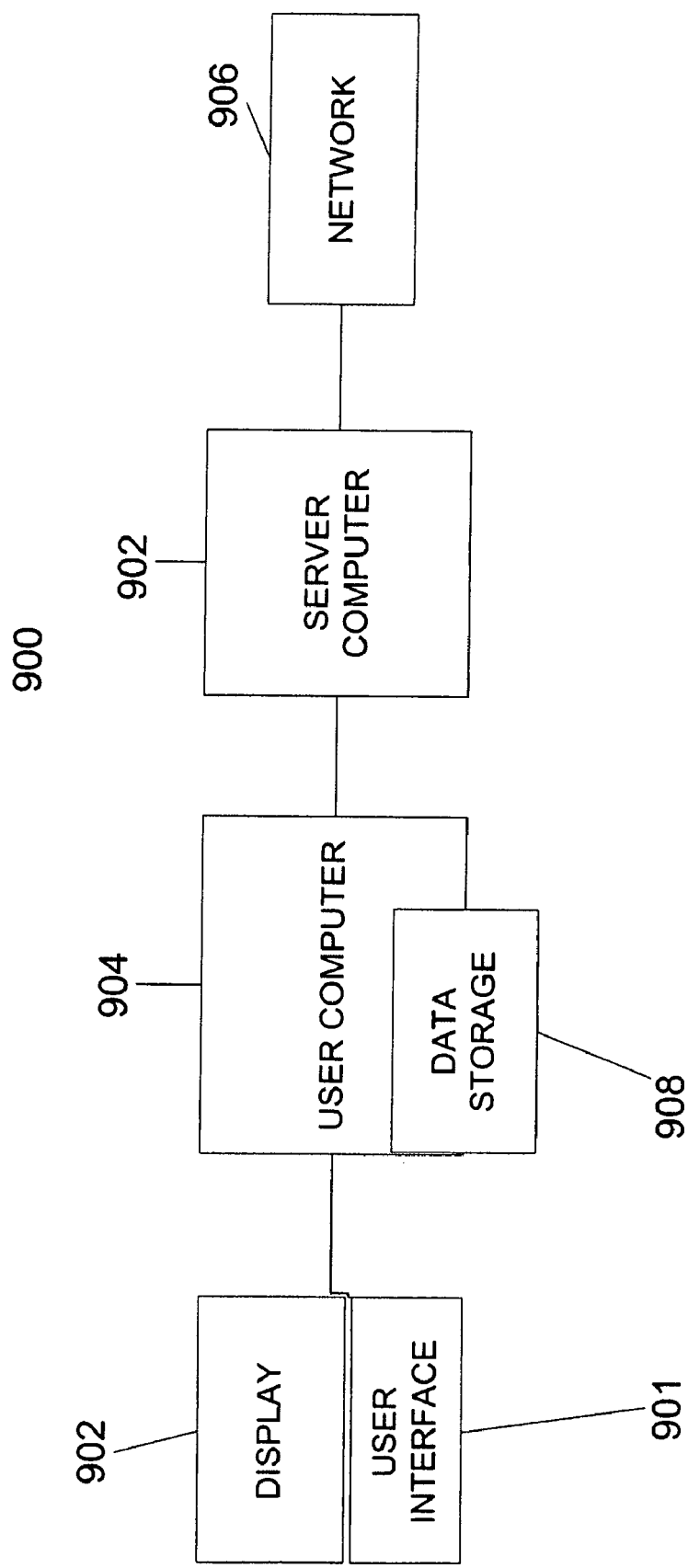
FIG. 9 is block diagram of one embodiment of an architecture that can be used to practice aspects of the disclosed embodiments.

The disclosed embodiments may also include software and computer programs incorporating the process steps and instructions described above that are executed in different computers. FIG. 9 is a block diagram of one embodiment of a typical apparatus 900 incorporating features of the disclosed embodiments that may be used to practice aspects of the invention. For example, in one embodiment, a computer system 904 may be linked to another computer system 902, such that the computers 904 and 903 are capable of sending information to each other and receiving information from each other. As shown in FIG. 9, these computer systems are defined as a User Computer 904 and Server Computer 902. In alternative embodiments, any suitable, and any suitable number of computer systems or structures can be communicatively coupled together to practice the aspects of the invention. In one embodiment, computer systems 904 and 902 could include or be adapted to communicate with a network 904, which in one embodiment may comprise the Internet or any suitable network. Computer systems 904 and 902 can be linked together in any conventional manner including a modem, hard wire connection, or fiber optic link. Generally, information can be made available to both computer systems 904 and 902 using a communication protocol typically sent over a communication channel or through a dial-up connection on ISDN line. Computers 904 and 902 are generally adapted to utilize program storage devices embodying machine readable program source code which is adapted to cause the computers 904 and 902 to perform the method of the disclosed embodiments. The program storage devices incorporating features of the disclosed embodiments may be devised, made and used as a component of a machine utilizing optics, magnetic properties and/or electronics to perform the procedures and methods of the disclosed embodiments. In alternate embodiments, the program storage devices may include magnetic media such as a diskette or computer hard drive, which is readable and executable by a computer. In other alternate embodiments, the program storage devices could include optical disks, read-only-memory ("ROM") floppy disks and semiconductor materials and chips.

Computer systems 904 and 902 may also include a microprocessor for executing stored programs. For example, either or both computers 904 and 902 may include one or more data storage devices 908 as its program storage device for the storage of information and data. The computer program or software incorporating the processes and method steps incorporating features of the disclosed embodiments may be stored in one or more computers 904 and 902 on an otherwise conventional program storage device. In one embodiment, computers 904 and 902 may include or be coupled to at least one user interface 901, and a display interface 902 from which features of the disclosed embodiments can be accessed. In one embodiment, the user interface 901 and the display interface 902 can comprise a single interface device, such as for example a graphical user interface. The user interface 901 and the display interface 902 can be adapted to allow the input of queries and commands to the system, as well as present the results of the commands and queries.

In one embodiment, a user interface of the disclosed embodiments can be configured to capture this attribute information. The user interface can provide for creation of the attribute in connection with the filter dictionary. The user interface will allow the user to define the algorithm(s) to be used in connection with the filter dictionary term and the dictionaries with which the algorithm(s) can be used. The algorithm can be defined in any suitable manner that is understood by the management system of which the filter dictionary is a part. In this situation, the user would only need to select the search criteria and select to execute algorithms for all cases, in which instance the defined search algorithms would be carried out for source data mapped to the dictionary terms. In the above example, the user interface would allow the user to select "acute Pancreatitis" as the search criteria and enable the execution for all cases. The search carried out would generally comprise selecting all cases mapped to any narrow term in union with all cases mapped to the intersection of the broad term categories, which in this example are the sign/symptom terms and relevant lab value terms.

The disclosed embodiments provide a centralized, globally available repository of dictionary and associated verbatim terms. Information in the repository is accessible through advanced searching and classification algorithms. This provides a global facility to standardize terminology use across dictionaries, computer applications, time and organizations. Since the number of dictionaries, including their organization and use can vary considerably, different dictionaries can exist for different types of information. The disclosed embodiments provide access to any number of dictionaries, including multiple versions of the same dictionary, any numbers of levels of hierarchy and custom or commonly used dictionaries. A base dictionary is defined for use with a thesaurus management system, for example, and a filter dictionary for the particular context is defined. Data is entered and loaded and the trial data is coded to the base dictionary. The data in the filter dictionary can then be used to find source data satisfying specific conditions using a pre-defined and deterministic set of mappings between the filter dictionary and the corresponding base dictionary. The filter system of the disclosed embodiments provides for the identification of complex data conditions in seemingly unrelated clinical data with the help of the terminology defined in the filter. The user pre-defines a series of relationships between dictionary terms and thus has a pre-determined way to retrieve data.

What is claimed is:

1. A non-transitory computer-readable storage medium storing computer executable instructions that when executed by a computer cause the computer to perform a method, the method comprising:

defining a plurality of terms for use in conjunction with a medical study where the terms are stored according to a series of relations and the relations corresponding to the terms indicate an association from a term to at least one other of the plurality of terms;

defining a primary level of medical relations for at least one group of terms taken from the plurality of terms and storing the at least one group of terms, including the relations corresponding to each term;

providing a match term defined by the group of terms;

defining a secondary level of medical relations including a plurality of category terms to be associated with one or more of the plurality of terms, where defining the secondary level of medical relations includes defining broad scope relation links and narrow scope relation links between the match term and the at least one group of terms taken from the plurality of terms, and where defining the secondary level of relations includes defining relationships between the match term and at least one term taken from the at least one group of terms that have no obvious linguistic relationship to each other;

mapping one or more terms from the plurality of terms to a category term, where the one or more terms do not share a relationship link with other one or more terms from the plurality of terms but with the category term;

querying a memory of data from the study to find occurrences of the category term as defined by the secondary level of relations of the mapped terms.

2. The computer-readable storage medium of claim 1, where the method comprises defining an occurrence of a match as a defined combination of selected terms.

3. The computer-readable storage medium of claim 1, where the method comprises defining a plurality of further levels of relations between the match term and the at least one group of terms taken from the plurality of terms.

4. A method, comprising:

receiving a query that includes a match term and one or more filter conditions;

evaluating the query against a plurality of clinical terms stored in a base dictionary, stored on a computer readable storage medium, where the plurality of clinical terms are aggregated using a first level of medical relations, where in the first level of medical relations clinical terms are linked to at least one other term in the plurality of clinical terms;

determining an intermediate result set that is based, at least in part, on clinical terms of the plurality of clinical terms that are linked to the match term in the base dictionary;

mapping the filter conditions to the match term, where the one or more filter dictionary terms do not share a relationship link with other one or more filter dictionary terms but with the filter conditions;

accessing a filter dictionary to filter the intermediate result set based, at least in part, on the one or more filter conditions to select a filtered result, where the one or more filter conditions employs a second level of medical relations stored in a filter dictionary that specify a broad scope of relevance and a narrow scope of relevance between clinical terms that have no obvious linguistic relationship to each other in the base dictionary and the mapped filter dictionary terms in the filter dictionary without defining a relationship between clinical terms and the mapped filter dictionary terms, where the broad scope of relevance causes a broader filtered result based on the filter conditions and the narrow scope of relevance causes a narrower filtered result based on the filter conditions; and returning the filtered result based, at least in part, on the filter conditions.

5. The method of claim 4, where employing the narrow scope causes the clinical terms of the filtered result to be directly related to a filter dictionary term.

6. The method of claim 4, where employing the broad scope causes the clinical terms of the filtered result to be indirectly related to a filter dictionary term.

7. A system, comprising:

a base dictionary, stored on a computer readable storage medium, comprising clinical terms from a study linked to one another;

a filter dictionary comprising filter clinical dictionary terms;

a set of filter links mapping clinical terms to the filter clinical dictionary terms, a filter link having an associated scope of relevance describing a level of relevance between the linked filter dictionary term and clinical term, where at least one scope of relevance is a narrow scope of relevance and at least one scope of relevance is a broad scope of relevance, the filter links defining a level of medical relationships between a clinical term and at least one other clinical term taken from the at least one clinical terms that have no obvious linguistic relationship to each other; and a query processing unit configured to receive a clinical match term and one or more filter conditions, where the filter conditions are searchable based on a corresponding scope of relevance and to query a memory of data from study to return results that include the clinical match term as filtered by the filter conditions.

8. The system of claim 7, where a filter link with the narrow scope of relevance describes a filter clinical dictionary term that establishes that at least two clinical terms are synonymous.

9. The system of claim 7, where a filter link with the broad scope of relevance describes a filter clinical dictionary term that establishes that a first clinical term is related to a second clinical term because the first clinical term is a symptom, a sign, a lab value, or a treatment related to the second clinical term.

10. The system of claim 7, where the query processing unit is configured to receive at least two filter conditions, where the at least two filter conditions comprise at least two different scopes of relevance.

11. The system of claim 7, where the filter clinical dictionary terms store groupings of clinical terms that share unique attributes, properties, or linguistic relevance.

* * * * *

UNITED STATES PATENT AND TRADEMARK OFFICE
CERTIFICATE OF CORRECTION

| | | |
|---|---|---|
| PATENT NO. | : 7,912,864 B2 | Page 1 of 1 |
| APPLICATION NO. | : 11/861237 | |
| DATED | : March 22, 2011 | |
| INVENTOR(S) | : Rejndrup | |

It is certified that error appears in the above-identified patent and that said Letters Patent is hereby corrected as shown below:

In column 5, line 66, delete "termininolgies" and insert -- terminologies --, therefor.

In column 7, line 49, after "307D" insert -- . --.

In column 9, line 40, delete "FIG. A4" and insert -- FIG. 4 --, therefor.

In column 11, line 25, delete "FIG. 8.," and insert -- FIG. 8, --, therefor.

In column 11, line 40, delete "11" and insert -- II --, therefor.

Signed and Sealed this
Fourth Day of October, 2011

David J. Kappos
*Director of the United States Patent and Trademark Office*